United States Patent [19]

Karami

[11] 4,055,184
[45] Oct. 25, 1977

[54] ABSORBENT PAD

[75] Inventor: Hamzeh Karami, Crystal Lake, Ill.

[73] Assignee: Colgate-Palmolive Company, New York, N.Y.

[21] Appl. No.: 684,544

[22] Filed: May 10, 1976

[51] Int. Cl.² .................................................. A61F 13/16
[52] U.S. Cl. ............................ 128/287; 128/290 R; 128/284
[58] Field of Search .............. 128/284, 287, 290 R, 128/290 P, 296; 260/17.4, 29.6 ST

[56] References Cited

U.S. PATENT DOCUMENTS

| 3,425,971 | 2/1969 | Gugliemelli | 260/17.4 |
| 3,661,815 | 5/1972 | Smith et al. | 260/17.4 |
| 3,794,029 | 2/1974 | Dulle | 128/285 |
| 3,814,101 | 6/1974 | Kozak | 128/287 |
| 3,871,037 | 3/1975 | Willington | 128/287 X |
| 3,888,256 | 6/1975 | Studinger | 128/296 |
| 3,903,889 | 9/1975 | Torr | 128/287 |
| 3,927,673 | 12/1975 | Taylor | 128/287 |

Primary Examiner—Aldrich F. Medbery

[57] ABSTRACT

An absorbent pad such as a disposable diaper, sanitary napkin, bandage or the like for use in contact with the skin for absorbing body fluids and having a mass of material including a solid, finely-divided mixture of a hydrolyzed starch polyacrylonitrile graft copolymer in acidic form comprised of 0.6 to 2 parts by weight of hydrolyzed grafted polyacrylonitrile in acidic form per part by weight of starch and a non-irritating and non-toxic water-soluble basic material, the relative proportion of base to copolymer being from 1:4 to 1:1 by weight.

7 Claims, 5 Drawing Figures

ABSORBENT PAD

This invention relates to an absorbent pad for use in contact with the skin for absorbing body fluids, for example, a disposable diaper, sanitary napkin, bandage or the like, and having an improved capacity for absorbing and retaining liquid such as urine even when placed under moderate pressure.

It has previously been proposed to employ absorbent pads containing various polymers and gums including among others hydrolyzed starch-polyacrylonitrile graft copolymers as described in U.S. Pat. Nos. 3,425,971 and 3,661,815, which polymers are said to increase the urine absorbency of the pads.

The present invention provides an absorbent pad for use in contact with the skin comprising a water pervious facing layer for contacting the skin, a water-impervious backing sheet bonded to the facing layer around its periphery to form a container, and disposed within said container an absorbent mass of solid finely-divided mixture of (1) a completely hydrolyzed starch-polyacrylonitrile graft copolymer in acidic form containing 0.6 to 2 parts by weight of grafted hydrolyzed polyacrylonitrile in acidic form per part by weight of starch and (2) a non-irritating and non-toxic water-soluble basic material, the relative proportion of base to copolymer being from 1:4 to 1:1 by weight. The pads of the present invention display when subjected to moderate pressure, that is, up to about 3 p.s.i., a substantially greater absorptive capacity for liquids such as urine than do similar pads which include previously hydrolyzed starch-polyacrylonitrile graft copolymer without basic material.

Figure 1:
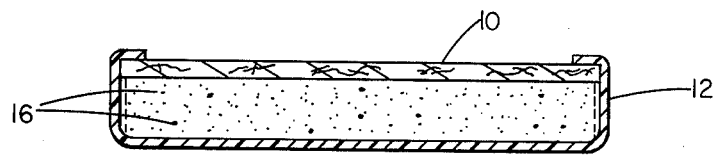
FIG. 1 is a view in cross-section showing one embodiment of the present invention.

In the embodiment shown in FIG. 1, the absorbent pad comprises a facing layer 10 of fibrous material which preferably is a mixture of long, textile-length cellulosic fibers such as cotton or staple rayon, the fibers generally being from ½ to 2 inches in length, together with short cellulosic fibers such as cotton linters or wood pulp or paper fibers, the short fibers being ¼ inch or less in length and being present in an amount from 75–98% by weight of the total fibers in the facing layer, the total weight of the facing layer being from 10 to 40 grams/sq. yard. Other woven or non-woven fabrics may also be employed as the facing layer if desired, in particular a bonded web of textile length fibers in which the binder is confined to a pattern of spaced zones leaving the intermediate areas free from binder and readily pervious to liquids. The function of the facing layer 10 which contacts the skin of the user during use of the pad is to provide a smooth, soft non-irritating surface which has sufficient coherent strength to maintain its integrity either wet or dry so that it can be cleanly and completely removed from the skin after use and which is sufficiently open and porous so as to be readily penetrated by the body fluids to permit their absorption by the body of the pad. The fibers of the facing layer 10 may be treated with a wetting agent such as an anionic surface-active agent to enhance their wettability and the penetration of such layer by body fluids, if desired.

Facing layer 10 is bonded along its margins to a flexible water-impervious backing sheet 12 which may be in the form of a sheet of film of plastic material such as polyethylene, or a sheet of waterproof paper, the facing layer and backing sheet together forming an envelope or container within which is disposed the main body of the absorbent pad. Bonding of facing layer 10 to backing sheet 12 can be carried out simply by heat sealing or fusing the margins together when the backing sheet is thermoplastic, or a conventional adhesive composition can be employed for bonding purposes. In the embodiment of FIG. 1, this main body consists simply of a solid finely-divided admixture 16 of completely hydrolyzed starch-polyacrylonitrile graft copolymer in acidic form containing 0.6 to 2 parts by weight of grafted hydrolyzed polyacrylonitrile in acidic form per part by weight of starch and a water-soluble non-irritating and non-toxic solid basic material such as sodium bicarbonate. The proportion of basic material to graft copolymer may vary from 1:4 to 1:1 by weight and the total amount of the admixed copolymer and basic material may vary from 2 to 80% by weight of the total absorbent pad including both facing layer and backing sheet. The graft copolymer and solid basic material for best results are in finely-divided form, capable of passing a No. 16 sieve of the U.S. Standard Sieve Series. The body of admixture 16 may be applied by sprinkling or otherwise depositing it upon either of the opposing faces of facing layer 10 or backing sheet 12 with or without previous moistening of either to prevent loss by dusting. It is also possible to dissolve the basic material in a small amount of water and apply it in the form of an aqueous solution, e.g., by spraying, to the surface of the layer of the solid hydrolyzed graft copolymer particles in acidic form on the surface of either facing layer 10 or backing sheet 12. Upon drying, the basic material is deposited in solid finely-divided form in the desired location in close association with the solid particles of copolymer. The total thickness of the main body can be from 2 to 6 mm.

Figure 2:
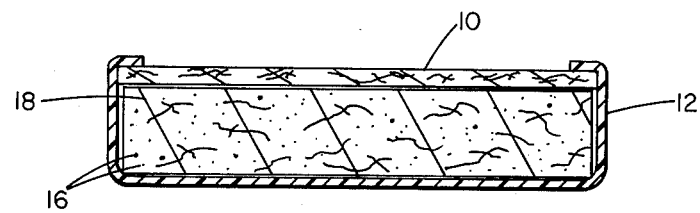
FIG. 2 is a view in cross-section showing another embodiment.

In another embodiment of the invention shown in FIG. 2 the main body 18 of the absorbent pad is in the form of a water-absorbent mass of particulate material such as one or more highly porous webs or batts of cellulosic fibers such as fiberized wood pulp, wadding made of cotton linters, layers of creped tissue, or a mass of shredded polyurethane foam particles, body 18 having a basis weight from 10 to 20 lbs. per 2880 sq. ft., the finely-divided admixture 16 being disposed throughout body 18 and distributed among the other particles or fibers; the body 18, before dispersion of mixture 16 throughout its mass, has a basis weight from 10 to 20 lb. per 2880 sq. ft. As in the case of the embodiment of FIG. 1, the total amount of mixture 16 can vary from 2 to 80% by weight of the total absorbent pad. Mixture 16 can be intermingled with or dispersed into the mass of particulate material before or after the latter is formed into body 18; for example, mixture 16 can be intermingled with shredded particles of polyurethane foam before it is formed into body 18, or it can be mixed with a mass of fibrous material before the latter is formed into a web or batt.

Figure 3:
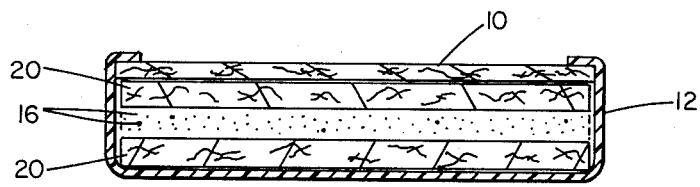
FIG. 3 is a view in cross-section showing a third embodiment.

Alternatively, body 18 may be formed as shown in FIG. 3 by plying up or laminating a plurality of individual layers or batts of fibrous material 20 such as cellulosic fibers and mixture 16 can be applied by sprinkling between the layers or on the faces thereof with or without moistening of the layers with water, in a manner similar to that used in making the embodiment of FIG. 1.

Figure 4:
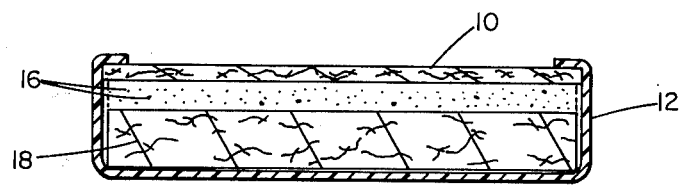
FIG. 4 is a view in cross-section showing a fourth embodiment.

In the embodiment of the invention shown in FIG. 4, the solid finely-divided mixture 16 of completely hydrolyzed grafted starch-polyacrylonitrile copolymer in acidic form and solid water-soluble basic material can be concentrated at the upper face of body 18, for example, by sprinkling the mixture on the surface of body 18 after the formation of the latter and before facing layer 10 is applied. Alternatively, the mixture 16 can be applied, if desired, to the inner face of facing layer 10 before assembling layer 10 with body 18. In either case, a small amount of water can be used either to moisten the layer or to dissolve the basic material to prevent loss by dusting during manufacture.

Figure 5:
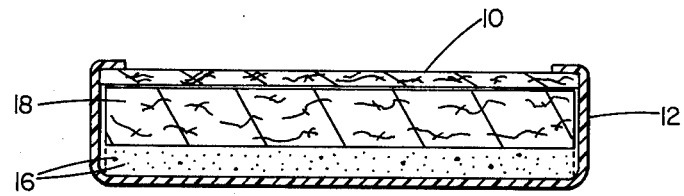
FIG. 5 is a view in cross-section showing a fifth embodiment.

In still a fifth embodiment of the invention, shown in FIG. 5, the solid finely-divided mixture 16 can be concentrated at the bottom face of body 18 by applying it thereto as described above or by applying it to the upper face of backing sheet 12 before assembly with body 18.

In the case of each of the embodiments of FIGS. 3 to 5 inclusive, the weight of the mixture can be from 2 to 80% of the total weight of the absorbent pad, including both facing layer and backing sheet.

The water-soluble basic material of choice is sodium bicarbonate because of its low cost and non-irritating and non-toxic properties, but any other solid water-soluble non-irritating and non-toxic basic material capable of producing in aqueous solution with the associated hydrolyzed grafted starch-polyacrylonitrile copolymer in acidic form a pH from 6.5 to 9.0 can be used. Among such basic materials are mono- or disodium phosphate, sodium borate, potassium bicarbonate, disodium phthalate, and the like.

The absorbent pads of the present invention, when under moderate pressure such as 2-3 pounds per sq. inch, display a remarkably improved absorption capability for body fluids such as urine as compared to similar pads containing no copolymer or basic material or containing previously hydrolyzed copolymer prepared for example as described in U.S. Pat. No. 3,661,815. This absorptive capability is of particular importance in the case of disposable diapers which are required to function when subjected to the pressure of an infant's body.

What is claimed is:

1. An absorbent pad for use in contact with the skin comprising a water pervious facing layer for contacting the skin, a water-impervious backing sheet bonded to the facing layer around its periphery to form a container, and disposed within said container an absorbent mass comprising a solid finely-divided mixture of (1) a completely hydrolyzed starch-polyacrylonitrile graft copolymer in acidic form containing 0.6 to 2 parts by weight of grafted hydrolyzed polyacrylonitrile per part by weight of starch and (2) a non-irritating and non-toxic water-soluble basic material, the relative proportion of base to copolymer being from 1:4 to 1:1 by weight.

2. An absorbent pad as claimed in claim 1 in which said mass is in the form of a highly porous batt of cellulosic fibers carrying said finely-divided mixture dispersed therein.

3. An absorbent pad as claimed in claim 1 in which said mass is in the form of a highly porous batt of cellulosic fibers carrying said finely-divided mixture disposed adjacent one face of said batt.

4. An article as claimed in claim 1 in which said mass is in the form of a highly porous batt of cellulosic fibers carrying said finely-divided mixture disposed between said facing layer and said batt.

5. An absorbent pad as claimed in claim 1 in which said mass is in the form of a highly porous batt of cellulosic fibers carrying said finely-divided mixture disposed between said backing sheet and said batt.

6. An absorbent pad as claimed in claim 1 in which said mass is in the form of a plurality of highly porous batts of cellulosic fibers carrying said finely-divided mixture disposed between said batts.

7. An absorbent pad as claimed in claim 1 in which said mass is in the form of a mass of shredded polyurethane foam particles carrying said finely-divided mixture dispersed in said mass.

* * * * *